United States Patent
Oku et al.

(10) Patent No.: US 7,285,187 B2
(45) Date of Patent: Oct. 23, 2007

(54) METHOD OF PURIFYING PROPYLENE OXIDE

(75) Inventors: Noriaki Oku, Ichihara (JP); Toshio Nakayama, Sodegaura (JP); Koji Shinohara, Ichihara (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 10/504,548

(22) PCT Filed: Feb. 7, 2003

(86) PCT No.: PCT/JP03/01287

§ 371 (c)(1),
(2), (4) Date: Aug. 13, 2004

(87) PCT Pub. No.: WO03/068761

PCT Pub. Date: Aug. 21, 2003

(65) Prior Publication Data

US 2005/0092593 A1 May 5, 2005

(30) Foreign Application Priority Data

Feb. 15, 2002 (JP) ............... 2002-038202

(51) Int. Cl.
*B01D 3/40* (2006.01)
*B01D 3/42* (2006.01)
*C07D 301/32* (2006.01)
*C07D 303/04* (2006.01)

(52) U.S. Cl. ............... 203/3; 203/68; 203/98; 203/64; 549/541

(58) Field of Classification Search ............... 203/3, 203/68, 100, 98, 64; 549/541
See application file for complete search history.

(56) References Cited

U.S. PATENT DOCUMENTS

| | | | |
|---|---|---|---|
| 3,338,800 A | | 8/1967 | Binning et al. |
| 3,607,669 A | | 9/1971 | Jubin, Jr. |
| 3,632,482 A | * | 1/1972 | Hoory et al. ............... 203/56 |
| 3,843,488 A | | 10/1974 | Schmidt et al. |
| 3,909,366 A | * | 9/1975 | Schmidt et al. ............... 203/69 |
| 4,379,025 A | * | 4/1983 | Yudovich et al. ............... 203/14 |
| 4,437,939 A | * | 3/1984 | Bhise et al. ............... 203/14 |
| 5,000,825 A | * | 3/1991 | Shih et al. ............... 203/3 |
| 5,133,839 A | | 7/1992 | Shih |

(Continued)

FOREIGN PATENT DOCUMENTS

| | | |
|---|---|---|
| EP | 0 675 119 A2 | 10/1995 |
| EP | 0 685 472 A | 12/1995 |
| WO | WO 01/83468 A | 11/2001 |

OTHER PUBLICATIONS

Coulson et al, "Chemical Engineering" vol. 2, Unit Operations, Third Edition, p. 478.*
Supplementary European Search Report dated Jan. 19, 2006.

*Primary Examiner*—Virginia Manoharan
(74) *Attorney, Agent, or Firm*—Sughrue Mion Pllc.

(57) ABSTRACT

A process for purifying propylene oxide characterized by subjecting a liquid reaction mixture containing propylene oxide, and water, hydrocarbons and oxygen-containing organic compounds as impurities obtained by reacting cumene hydroperoxide with propylene to extractive distillation using an extractant of a hydrocarbon having 7 to 20 carbon atoms with an extractive distillation column, and controlling a concentration of propylene glycol in the extractant supplied to the extractive distillation column to 20% by weight or less.

4 Claims, 1 Drawing Sheet

U.S. PATENT DOCUMENTS 5,154,804 A * 10/1992 Marquis et al. ................ 203/63
5,262,017 A * 11/1993 Meyer et al. .................. 203/64
5,319,114 A    6/1994 Gaffney et al.
5,830,324 A * 11/1998 Downs et al. .................. 203/1
6,500,311 B1 * 12/2002 Sawyer ........................ 203/44
6,736,941 B2 *  5/2004 Oku et al. ..................... 203/68

* cited by examiner

METHOD OF PURIFYING PROPYLENE OXIDE

TECHNICAL FIELD

The present invention relates to a process for purifying propylene oxide. More particularly, the present invention relates to an industrially advantageous process for purifying propylene oxide by subjecting a liquid reaction mixture containing propylene oxide obtained by reacting cumene hydroperoxide with propylene to extractive distillation using a hydrocarbon having 7 to 20 carbon atoms as an extractant, wherein the process can suppress deterioration of the capability of the extractant and reduce the cost regarding the extractant.

BACKGROUND ART

As a producing process of propylene oxide, a process in which cumene hydroperoxide with propylene is reacted, is known.

In the liquid reaction mixture obtained by the reaction, water, hydrocarbons, oxygen-containing organic compounds such as methanol, propionaldehyde, acetone and methyl formate as impurities, are contained in addition to propylene oxide as a target product. Therefore, multi-stage purification steps become necessary to separate and recover propylene oxide of high purity from the liquid reaction mixture.

In purification of propylene oxide, use of a hydrocarbon as an extractant is publicly known. For example, U.S. Pat. No. 3,843,488 discloses that an alkane such as octane is effective for removing hydrocarbons having 6 carbon atoms as impurities. Further, JP 50-007571 B discloses that an alkane such as octane is effective for removal of water. Furthermore, U.S. Pat. No. 5,133,839 discloses that a hydrocarbon such as octane is effective for removal of impurities such as methanol, propionaldehyde and acetone.

DISCLOSURE OF THE INVENTION

An object of the present invention is to provide an industrially advantageous process for purifying propylene oxide by subjecting a liquid reaction mixture containing propylene oxide obtained by reacting cumene hydroperoxide with propylene to extractive distillation using a hydrocarbon having 7 to 20 carbon atoms as an extractant, wherein the process can suppress deterioration of the capability of the extractant and reduce the cost regarding the extractant.

That is, the present invention relates to a process for purifying propylene oxide, which comprises:

subjecting a liquid reaction mixture containing propylene oxide obtained by reaction of cumene hydroperoxide with propylene, and water, hydrocarbons and oxygen-containing organic compounds as impurities to extractive distillation using a hydrocarbon having 7 to 20 carbon atoms as an extractant, with an extractive distillation column, and controlling a concentration of propylene glycol contained in the extractant supplied into the extractive distillation column to 20% by weight or less.

EXPLANATION OF SYMBOLS

Figure 1:
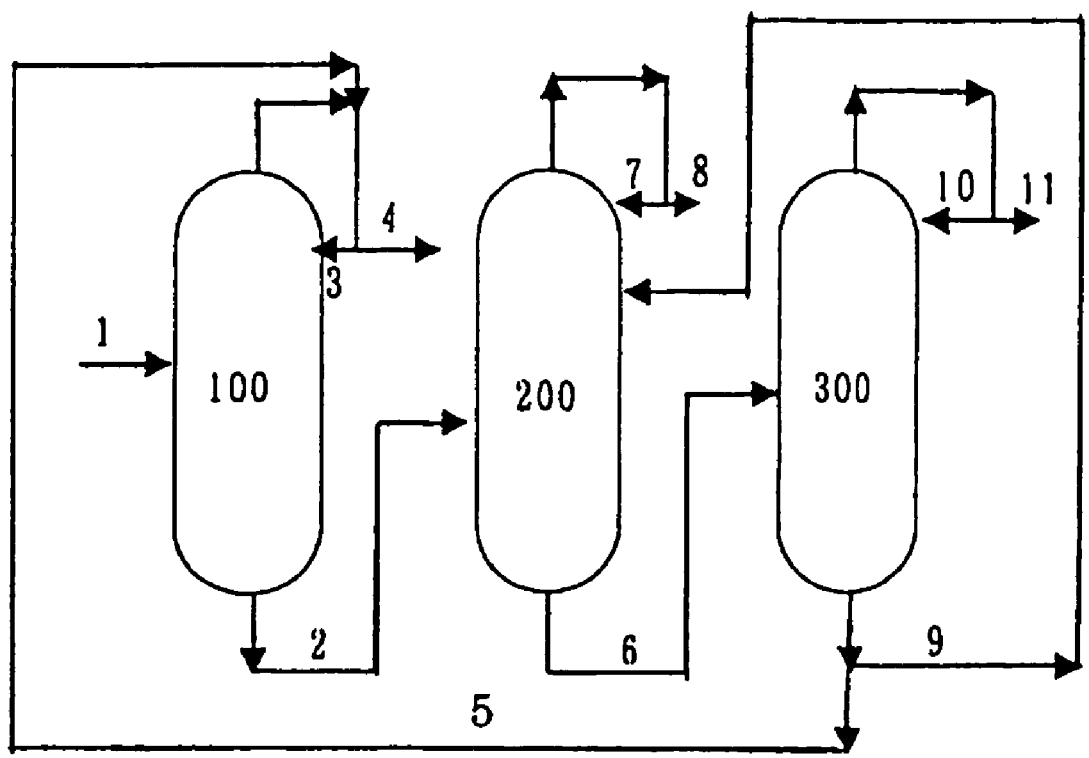
FIG. 1 is a FIGURE showing a flow of a purification process of the present invention.

100: Extractive distillation column, 200: Extractive distillation column, 300: distillation column 1. Line for supplying a propylene oxide raw material containing water, hydrocarbons and oxygen-containing compounds as impurities, 2. Bottom stream line of extractive distillation column (100), 3. Refluxing line of extractive distillation column (100), 4. Overhead stream line of extractive distillation column (100), 5. Extractant supplying line of extractive distillation column (100), 6. Bottom stream line of extractive distillation column (200), 7. Refluxing line of extractive distillation column (200), 8. Purified propylene oxide stream line, 9. Extractant supplying line of extractive distillation column (200), 10. Refluxing line of distillation column (300), 11. Overhead stream line of distillation column (300)

BEST MODE FOR CARRYING OUT THE INVENTION

A raw material liquid to be subjected to the purification process of the present invention is a liquid reaction mixture containing propylene oxide obtained by reaction of cumene hydroperoxide with propylene, and water, hydrocarbons and oxygen-containing organic compounds as impurities. Usually, the reaction is carried out in the presence of a catalyst under conditions under which the reaction temperature is 10 to 200° C., the pressure is 1 to 20 MPa, and the amount of propylene is 2 to 50 times, preferably 5 to 30 times by mole of that of cumene hydroperoxide. When the amount of propylene is below the above-described range, the reaction insufficiently proceeds or the yield of propylene oxide decreases, on the other hand, when the amount of propylene is above the above-described range, the production becomes disadvantageous in economical because of recovery cost and purge loss of unreacted propylene. After propylene in the liquid reaction mixture has been recovered by distillation, the recovered propylene is recycled to the reactor again. The liquid reaction mixture containing propylene oxide (hereinafter, sometimes referred to as "liquid raw material".) to be subjected to the purifying process of the present invention is obtained by subjecting a reaction liquid after recovery of propylene to crude distillation to separate propylene oxide from cumene and cumyl alcohol.

As hydrocarbons contained as the above-described impurities, saturated and unsaturated hydrocarbons having 3 to 7 carbon atoms can be listed.

Further, as oxygen-containing organic compounds contained as impurities, aldehydes such as propionaldehyde, alcohols such as methanol, ketones such as acetone, carboxylic acid esters such as methyl formate, and the like can be listed.

In the present invention, the liquid raw material is subjected to extractive distillation using a hydrocarbon having 7 to 20 carbon atoms as an extractant. As the extractant, linear saturated hydrocarbon such as n-heptane, n-octane, n-nonane, n-decane, n-undecane and n-dodecane, branched saturated hydrocarbon such as 2,2-dimethylpentane, 2,3-dimethylpentane, 2,2-dimethylhexane and 2,3-dimethyl hexane; unsaturated hydrocarbons thereof; and the like can be listed. In addition, these extractants can be used in any of a single and mixture thereof. From the industrial viewpoint, easily available saturated hydrocarbons having 7 carbon atoms are preferable.

The extractive distillation is a distillation method adding another component as an extractant to a mixture containing two components of which separation is difficult or impossible in usual distillation separation thereby changing a relative volatility of the original two components and making easy separation of the two components. Since methanol, water, acetaldehyde, hydrocarbons having 5 and 6 carbon atoms among impurities in propylene oxide are near to 1 in a relative volatility, these are difficult in separation by usual distillation. For example, in propylene oxide containing 0.1% by weight of methanol and 0.1% by weight of 1-hexene, when respective relative volatilities of those to propylene oxide are compared, under atmospheric pressure, the relative volatility of methanol is 1.1 and that of 1-hexene is 1.1. Since both relative volatilities are near to 1, it is shown that separation by distillation of these is difficult. Accordingly, it is difficult to industrially obtain propylene oxide having a sufficient purity by the usual distillation separation method. In such this case, there is used a method which includes carrying out separation adding a hydrocarbon having 7 to 20 carbon atoms as an extractant to enlarge relative volatilities to propylene oxide of methanol, water, acetaldehyde and the hydrocarbons.

However, it was found that when propylene glycol in the hydrocarbon having 7 to 20 carbon atoms as an extractant, exists at a certain concentration or higher, the effect of the extractant described above was markedly lost. In addition, the extractant is recycled, from the economical viewpoint, after separating propylene oxide and then purifying for separating impurities. However, when propylene glycol is contaminated in the extractant, it is not separated from the hydrocarbon having 7 to 20 carbon atoms since it has a boiling point higher than those of methanol, water, acetaldehyde, hydrocarbons having 6 carbon atoms, and it was re-supplied into the distillation column together with the extractant, accumulated and circulated. When it is re-supplied into the extractive distillation column, the concentration of the extractant decreases and the capability is deteriorated. Therefore, the amount of the extractant to be used increases and it lead to increase of energy cost for purification of the extractant.

Propylene glycol easily produced in the co-existence of propylene oxide and water, since it is produced during production or purification of propylene oxide.

As a method of decreasing the concentration of propylene glycol, separation methods such as distillation, adsorption, washing, still standing separation and extraction, can be listed, but washing is preferable from the economical viewpoint. For example, the concentration of propylene glycol in the extractant can be easily reduced because the extractant and water occurs phase separation through washing of the extractant by adding water to the extractant, and propylene glycol of water-soluble is extracted to water phase.

According to the preferable embodiment of the present invention, the concentration of propylene glycol in the hydrocarbon having 7 to 20 carbon atoms as the extractant for purifying propylene oxide is decreased to 20% by weight or less, preferably 10% by weight or less. Though the effect of the extraction becomes larger and the separation becomes easier in inverse proportion of the concentration of propylene glycol in the hydrocarbon having 7 to 20 carbon atoms as the extractant, when over 20% by weight, the effect of the extractant is killed and becomes near the same as that in no extractant.

One example of a flow of preferable embodiment of the present invention is shown in the drawing. A liquid raw material for purifying propylene oxide, containing water, hydrocarbons and oxygen-containing organic compounds as impurities is obtained by distilling and separating a liquid reaction mixture obtained through reaction of propylene with cumene hydroperoxide.

The liquid raw material is fed into an extractive distillation column 100 through a line 1. At the same time, n-heptane is fed as an extractant. The extractive distillation column 100 is a column for removing most of water and oxygen-containing organic compounds contained in the raw material, those are discharged as an overhead stream through a line 4, and as the bottom stream, n-heptane fed through a line 5 and propylene oxide fed through the line 1 are obtained. In addition, a part of the overhead stream may be returned through the line 3. The bottom stream of the extractive distillation column 100 is fed to an extractive distillation column 200 through a line 2, simultaneously n-heptane is fed to the extractive distillation column 200 through a line 9. Purified propylene oxide is obtained through a line 8 from the overhead, most of the hydrocarbons contained in the raw material and n-heptane as the extractant are obtained through a line 6 from the bottom. Further, a part of the overhead stream maybe returned through a line 7. The bottom stream obtained from the extractive distillation column 200 is fed to a distillation column 300 through a line 6, most of the hydrocarbons contained in the propylene oxide raw material are discharged through a line 11, and the bottom stream is recycled to the extractive distillation column 100 and/or 200 through 5 and/or 9, respectively. In the flow, when propylene glycol is contaminated, the extraction effect for removing the oxygen-containing compounds in the extractive distillation column 100, is damaged, further in the extractive distillation column 200, the extraction effect for removing the hydrocarbons, is markedly damaged. Furthermore, because propylene glycol has a higher in a boiling point than propylene oxide or other impurities, propylene glycol is accumulated and circulated together with the extractant, as the result, the volume of the extractant increases leading to disadvantages in economical.

Accordingly, a decrease of the concentration of propylene glycol in the extractant is very effective. The place for removing propylene glycol may be anywhere so far as the extractant exists, and it is preferable to wash and remove propylene glycol near the extractive distillation column 100 as a suitable place at which the effect of the present invention is put out at a maximum.

EXAMPLE

The present invention will be illustrated in detail referring to Examples below.

Examples 1 and 2, and Comparative Examples 1 and 2

When n-heptane was used as a extracting agent, comparisons of relative volatilities under the equilibrium condition of propylene oxide, and 2-methylpentane (hereinafter, 2MP), methanol (hereinafter, MTA), water and acetaldehyde (hereinafter, AA) as impurities, were carried out. As conditions, under atmospheric pressure, the relative volatilities were measured by adding n-heptane as an extractant of three to four times by weight of propylene oxide (PO) containing the impurities described above, and the relative volatilities at the concentrations of propylene glycol (hereinafter, PG) in n-heptane of 13% by weight and 36% by weight, respectively, ware measured and compared. Results are shown in Table 1.

TABLE 1

| | PG concentration in extractant (% By weight) | Relative volatility* | | | |
|---|---|---|---|---|---|
| | | 2MP | MTA | Water | AA |
| Comparative Example 1 | No use of extractant (Only PO containing impurities) | 1.5 | 0.7 | 0.9 | 1.5 |
| Example 1 | 0 | 0.3 | 2.9 | 11 | 2.7 |
| Example 2 | 13 | 0.3 | 1.2 | 1.2 | 1.3 |
| Comparative Example 2 | 36 | 0.4 | 0.5 | 0.4 | 0.9 |

*Relative volatility of each of components to PO

It is understood that though the relative volatilities of impurities become near 1 and usual separation is difficult when n-heptane is not used as an extractant, the volatilities of water, and AA and MTA as the oxygen-containing impurities become larger than that of PO and the separation becomes easy. In addition, 2MP as the hydrocarbon becomes smaller in volatility than PO, therefore, it is understood that separation of 2MP together with the extractant from PO becomes possible.

However, it is understood that, as the concentration of PG becomes large, the relative volatility become near 1, and when the concentration of propylene glycol becomes 36% by weight, with respect to 2MP, the separability decreases 1.5 times compared to 0 or 13% by weight of the PG concentration in the extractant, further, with respect to MTA, water and AA, volatilities thereof become small though volatilities thereof become essentially large depending on the effect of the extractant, therefore the separation from PO becomes difficult when PO is recovered from the overhead using the hydrocarbon as the extractant.

Accordingly, it is understood that in a case of extractive distillation using a hydrocarbon as an extractant, when the PG concentration exceeds 20% by weight, the effect of the extractant is markedly damaged.

INDUSTRIAL APPLICABILITY

As described above, according to the present invention, an process for purifying propylene oxide by subjecting a liquid reaction mixture containing propylene oxide obtained by reacting cumene hydroperoxide with propylene to extraction distillation using a hydrocarbon extractant having 7 to 20 carbon atoms, wherein the process for purifying propylene oxide, is extremely advantageous from the viewpoint of an industrial operation in particular, due to suppress deterioration in the capability of the extractant and reduce the cost regarding the extractant, can be provided.

The invention claimed is:

1. A process for purifying propylene oxide, which comprises:
   subjecting a liquid reaction mixture containing propylene oxide obtained by a reaction of cumene hydroperoxide with propylene, and water, hydrocarbons and oxygen-containing organic compounds as impurities to extractive distillation using a linear or branched saturated or unsaturated hydrocarbon having 7 to 20 carbon atoms as an extractant, with an extractive distillation column,
   recycling the extractant after separating propylene oxide and then purifying for separating the impurities, and
   controlling a concentration of propylene glycol contained in the extractant supplied into the extractive distillation column to 20% by weight or less, and
   wherein the liquid reaction mixture to be subjected to purification is one obtained by subjecting a reaction liquid obtained by reaction of cumene hydroperoxide with propylene after recovery of propylene to crude distillation to separate propylene oxide from cumene and cumyl alcohol.

2. The process according to claim 1, wherein the concentration of propylene glycol in the extractant is controlled to 20% by weight or less by washing the extractant with water.

3. The process according to claim 2, wherein the concentration of propylene glycol in the extractant is controlled to 10% by weight or less by washing the extractant with water.

4. The process according to claim 1, wherein the extractant is a linear or branched saturated hydrocarbon having 7 carbon atoms.

* * * * *